United States Patent [19]

Nakayama et al.

[11] 4,183,786

[45] Jan. 15, 1980

[54] PROCESS FOR PRODUCTION OF L-SERINE

[75] Inventors: Kiyoshi Nakayama, Sagamihara; Kazumi Araki; Yoshitake Tanaka, both of Machida, all of Japan

[73] Assignee: Kyowa Hakko Kogyo Co., Ltd., Japan

[21] Appl. No.: 855,328

[22] Filed: Nov. 28, 1977

[30] Foreign Application Priority Data

| Nov. 30, 1976 | [JP] | Japan | 51-143748 |
| Dec. 8, 1976 | [JP] | Japan | 51-147389 |
| Dec. 8, 1976 | [JP] | Japan | 51-147390 |
| Dec. 20, 1976 | [JP] | Japan | 51-153024 |

[51] Int. Cl.$^2$ ............................................. C12D 13/06
[52] U.S. Cl. ....................................... 435/116; 435/872
[58] Field of Search ................................. 195/29, 47

[56] References Cited

U.S. PATENT DOCUMENTS

| 3,843,441 | 10/1974 | Kubota et al. | 195/30 |
| 3,871,958 | 3/1975 | Nakazawa et al. | 195/29 |
| 3,880,741 | 4/1975 | Kageyama et al. | 195/29 |
| 4,060,455 | 11/1977 | Wagner et al. | 195/29 |

FOREIGN PATENT DOCUMENTS

50-48187  4/1975  Japan ......................................... 195/29

*Primary Examiner*—Lionel M. Shapiro
*Attorney, Agent, or Firm*—Craig and Antonelli

[57] ABSTRACT

A process for converting glycine to L-serine is effected by the use of an aqueous medium containing glycine and microbial cells of a mutant belonging to the genus Nocardia. The mutant is capable of converting glycine to L-serine and has no or lowered ability to decompose L-serine and/or a resistance to at least one metabolic antagonist selected from those of glycine, serine, methionine, glutamine, histidine, leucine, isoleucine, valine, purine, pyrimidine or folic acid. The L-serine is accumulated in the aqueous medium and is recovered therefrom.

11 Claims, No Drawings

PROCESS FOR PRODUCTION OF L-SERINE

BACKGROUND OF THE INVENTION

The present invention relates to a process for the production of L-serine from glycine.

L-serine is one of amino acids well known in the art and is in a great demand as material for medicament.

Heretofore, L-serine has been prepared using various methods. For example, it has been obtained by hydrolysis of proteins.

As for processes for the production of L-serine from glycine by fermentation, process using a microorganism belonging to the genus Nocardia is known as described in Japanese Patent Publication No. 9391/76. However, the yield of L-serine is poor.

Heretofore, it is reported on page 80 of the summary of lectures in Congress of Fermentation Technology, Japan 1975, that the increased yields of L-serine are obtained by culturing a mutant belonging to the species *Corynebacterium glycinophilum* and having both the ability to convert glycine to L-serine and the lowered ability to decompose L-serine.

As other prior methods of producing L-serine by fermentation, processes of culturing a strain belonging to the genus Arthrobacter, Corynebacterium, Brevibacterium, Escherichia, Micrococcus, Pichia, or Candida in a nutrient medium or in a nutrient medium containing glycine are known.

However, processes which have a high yield of L-serine are in demand for utilization in industrial practice.

The present inventors have studied a process for producing L-serine from glycine. As a result, it has been found that improved yield of L-serine may be attained by contacting glycine with microbial cells of a mutant belonging to the genus Nocardia and capable of converting glycine to L-serine, in an aqueous medium.

Further, it has been found that more improved yield of L-serine may be attained by presenting an additive such as hydrocarbon, alcohol, etc. to the medium.

Furthermore, it has been found that in the culturing of the mutant in the nutrient medium containing glycine, increased yields of L-serine are obtained by presenting phosphate to the medium at a high concentration.

SUMMARY OF THE INVENTION

In accordance with the present invention, increased yields of L-serine are obtained by converting glycine to L-serine in an aqueous medium containing microbial cells of a mutant belonging to the genus Nocardia and capable of converting glycine to L-serine.

The mutant has no or lowered ability to decompose L-serine and/or a resistance to at least one antagonist selected from those of glycine, serine, methionine, glutamine, histidine, leucine, isoleucine, valine, purine, pyrimidine or folic acid.

The conversion of glycine to L-serine is carried out during the culturing of the mutant in a nutrient medium containing glycine [Process (I)].

The conversion is also carried out by culturing the mutant in a nutrient medium to obtain microbial cells and presenting the microbial cells in an aqueous medium containing glycine [Process (II)].

Further, in the conversion of glycine to L-serine, more increased yields of L-serine are obtained by supplementing an additive such as hydrocarbon, alcohol, ketone, ether, ester, polyalcohol and the derivative of polyalcohols to the medium.

Further, in the culturing of the mutant in a nutrient medium containing glycine, more increased yield of L-serine is obtained in the culture liquor by supplementing phosphate to the medium to provide a medium containing phosphate at a high concentration of phosphate ions.

DESCRIPTION OF THE INVENTION

As the strain used in the present invention, any mutant belonging to the genus Nocardia and capable of converting glycine to L-serine, and having no or lowered ability to decompose L-serine and/or a resistance to at least one metabolic antagonists selected from those of glycine, serine, methionine, glutamine, histidine, leucine, isoleucine, valine, purine, pyrimidine or folic acid may be used.

Such a strain is obtained by endowing a strain of microorganism belonging to the genus Nocardia and capable of converting glycine to L-serine with no or lowered ability to decompose L-serine and/or a resistance to at least one metabolic antagonist mentioned above.

Further, the strain, is also obtained by endowing a strain of microorganism belonging to the genus Nocardia and having no or lowered ability to decompose L-serine and/or resistance to at least one metabolic antagonist mentioned above with the ability to convert glycine to L-serine.

Furthermore, the strain to be used in the present invention may have any other property for contributing to the L-serine productivity than the properties mentioned above.

In order to obtain mutants according to the present invention, standard procedures for inducing mutation may be followed such as irradiation with ultraviolet light, X-ray, Co 60, etc., or treatment with mutation inducing chemicals such as N-methyl-N'-nitro-N-nitrosoguanidine, etc. or the like.

A simple method to select a strain having no or lowered ability to decompose L-serine from the mixture obtained by mutation treatment is as follows:

The mixture is cultured on an agar plate having the minimum medium to form a colony. The resultant colony is cultured in a medium containing L-serine as a sole carbon source, a sole nitrogen source or a sole other nutrient source.

The strain that does not grow or does grow less than parent strain in the medium mentioned above, has no or lowered ability to decompose L-serine.

*Nocardia butanica* KY 7985 is an example of the mutant having a lowered ability to decompose L-serine, which is obtained from the resultant mixture by mutating the strain, *Nocardia butanica* ATCC 21197 according to the method mentioned above and the method mentioned later in detail.

A method to select a strain having a resistance to antagonist mentioned above from the mixture obtained by mutation treatment is as follows:

The mixture is cultured on an agar plate containing an antagonist and the minimum medium to form a colony.

The strain that does grow in the medium mentioned above has a resistance to the antagonist.

The strains listed below in Table 1 are examples of the mutant having a resistance to antagonist, which is obtained from the resultant mixture by mutating the strain, Nocardia butanica KY 7985 according to the method mentioned above and the method mentioned later in detail.

Table 1

| Private No. | FERM-P No. | NRRL No. | Antagonist |
|---|---|---|---|
| 20IMP-14 KY 7983 | 3764 | 11187 | trimethopurine (0.35) |
| 20MP-24 KY 7984 | 3765 | 11188 | 6-mercaptopurine (0.5) |
| 21SX-2 KY 7986 | 3766 | 11190 | serine hydroxamate (1) |
| 21GX-1 KY 7987 | 3767 | 11191 | glycine hydroxamate (1) |
| IE-36 KY 7988 | 3768 | 11059 | glycine hydroxamate (1) ethionine (5), norleucine (1) |
| IAU-3 KY 7989 | 3769 | 11192 | glycine hydroxamate (1) 6-azauracil (0.5) |
| 36MSF-2 KY 7990 | 3770 | 11193 | glycine hydroxamate (1) ethionine (5), methyl sulfone (5) |
| 36TRA-1 KY 7991 | 3771 | 11194 | glycine hydroxamate (1) ethionine (5), triazole alanine (1) |

Note:
Figure in the parentheses means concentration (mg/ml) of metabolic antagonist in the medium used for isolation of mutant.

The microbiological properties of the species of Nocardia butanica are described in Japanese Patent Publication No. 48673/72.

The above-noted mutants have been deposited with the Fermentation Research Institute, Agency of Industrial Science and Technology, Chiba-ken, Japan.

The strain KY-7985 is deposited under FERM-P No. 3782 and the other strains are deposited under FERM-P Nos. shown in Table 1.

These mutants have also been deposited with the Northern Regional Research Laboratory, 1815 North University Street, Peoria, Ill.

The strain KY 7985 has been accorded accession number NRRL 11189 and the other strains have been accorded accession numbers shown in Table 1.

Examples of metabolic antagonist are shown in Table 2.

TABLE 2

Example of Antagonist

Glycine: glycine-hydroxamate, amino methylsulfonic acid, chloromethyl-glycine, glycidic acid, N-methyl-glycine Serine: serine-hydroxamate, D-serine, homoserine Methionine: ethionine, tri-fluoro-methionine, α-methyl-methionine, methionine-hydroxamate, selenomethionine Glutamine: methionine-sulfone, methionine sulfoximine, azaserine, alanosine, duazomycin Histidine: thiazole-alanine, triazole-alanine, aminomethyl-triazole, α-methyl-histidine, histidine-hydroxamate Leucine: norleucine, tri-fluoroleucine, azaleucine, leucine-hydroxamate Isoleucine: thiaisoleucine, O-methyl-threonine, isoleucine-hydroxamate, D-isoleucine, norleucine Valine: norvaline, valine-hydroxamate, D-valine norleucine Purine: 6-mercaptopurine, 8-azaguanine, 2-fluoroadenine Pyrimidine: 5-fluorouracil, 2-thiouracil, 5-fluorocitosine, 6-azauracil Folic acid: amethopterin, aminopterin, trimethoprim, pyrimethamine The strain KY 7985, NRRL 11189 is obtained in the following manner. Microbial cells of the parent strain, i.e. Norcardia butanica ATCC 21197, are suspended at a concentration of about $10^8$ cells per ml, in 0.1 M-Tris-maleate buffer solution (pH 6.0). To the suspension is added 0.5 mg/ml of N-methyl-N'-nitro-N-nitrosoguanidine and the mixture is allowed to stand at room temperature for 30 minutes. Then the resultant suspension is smeared on an agar plate of a nutrient medium comprising 0.5 g/dl glucose, 0.5 g/dl yeast extract, 1 g/dl peptone, 1 g/dl meat extract, 0.5 g/dl NaCl and 2 g/dl agar (pH 7.2) and incubated at 30° C. for 2 days to form colonies. Cells of the resulting colonies are smeared on an agar plate of a minimum medium comprising 0.5 g/dl glucose, 0.2 g/dl $(NH_4)_2SO_4$, 0.15 g/dl $KH_2PO_4$, 0.05 g/dl $K_2HPO_4$, 0.05 g/dl $MgSO_4 \cdot 7H_2O$, 0.01 g/dl NaCl, 0.001 g/dl $FeSO_4 \cdot 7H_2O$, 0.001 g/dl $MnSO_4 \cdot nH_2O$, 0.001 g/dl $CaCl_2 \cdot 2H_2O$, 100 μg/l biotin, 1 mg/l thiamine hydrochloride, and 2 g/dl agar (pH 7.2) and also on an agar plate of a medium having the same composition as the minimum medium described above except using 0.2 g/dl L-serine instead of $(NH_4)_2SO_4$.

The strains having an ability to produce L-serine in a good yield are selected from those strains which do not grow on the latter medium, but do grow on the agar plate of the former medium, i.e. minimum medium.

The strain, Nocardia butanica KY 7985, NRRL 11189 is one of them.

The mutants shown in Table 1 are obtained in the following manner from the strain, Nocardia butanica KY 7985, NRRL 11189 as the parent strain. Microbial cells of the parent strain, i.e. Nocardia butanica KY 7985, NRRL 11189 are suspended at a concentration of about $10^8$ cells per ml, in 0.1 M Tris-maleate buffer solution (pH 6.0). To the suspension is added N-methyl-N'-nitro-N-nitrosoguanidine at a concentration of 0.5 mg/ml and the suspension is allowed to stand at room temperature for 30 minutes.

Then the suspension is diluted and the diluent is smeared on the agar plate of the medium having the same composition as the above-mentioned minimum medium except further containing the antagonist at a concentration shown in Table 1 and incubated at 30° C. for 2-10 days.

Thus, the mutants shown in Table 1 are selected from colonies which grow on the medium. The mutants are distinguished from the parent strain in possession of a resistance to the metabolic antagonists.

It may be determined by one or more of the following methods whether the mutant has a lowered ability to decompose L-serine compared with that of the parent.

A selected strain is cultured in a nutrient medium containing neither glycine nor L-serine in order to confirm that the strain does not produce L-serine. Then the strain is cultured in a nutrient medium containing not glycine but L-serine in order to determine the ability to decompose L-serine. After the completion of culturing, if the amount of L-serine remaining in the culture liquor is larger than that of the parent strain, the strain has no or lowered ability to decompose L-serine.

As other methods, logarithmic phase cells, stational phase cells, extract solution from cells or disrupted cells are incubated in an aqueous medium containing L-serine for an appropriate period of time. Then, the amount of L-serine in the mixture is determined and compared with that of L-serine at the start of the incubation.

It is understood from the following experiments that *Nocardia butanica* KY 7985 has the lowered ability to decompose L-serine.

EXPERIMENT 1

The strain of *Nocardia butanica* KY 7985, NRRL 11189 is cultured on an agar slant of the medium (pH 7.2) containing 0.5 g/dl glucose, 0.5 g/dl yeast extract, 2 g/dl peptone, 0.5 g/dl NaCl, and 2 g/dl agar at 30° C. for 2 days.

One loopful of the resulting seed culture is inoculated into 7 ml of a seed medium (pH 7.2) containing 4 g/dl glucose, 0.15 g/dl $KH_2PO_4$, 0.05 g/dl $K_2HPO_4$, 0.05 g/dl $MgSO_4 \cdot 7H_2O$, 0.3 g/dl urea, 50 µg/dl biotin, 0.5 g/dl yeast extract and 2 g/dl peptone in a large test tube (20 mm × 190 ml). Culturing is carried out with shaking at 30° C. for 24 hours.

0.25 ml of the resulting seed culture is inoculated into 5 ml of medium containing L-serine having the following composition in a large test tube:

glucose: 5 g/dl
$(NH_4)_2SO_4$: 0.2 g/dl
urea: 0.2 g/dl
$KH_2PO_4$: 0.15 g/dl
$K_2HPO_4$: 0.05 g/dl
$MgSO_4 \cdot 7H_2O$: 0.05 g/dl
NaCl: 0.01 g/dl
$FeSO_4 \cdot 7H_2O$: 0.001 g/dl
$MnSO_4 \cdot nH_2O$: 0.001 g/dl
biotin: 50 µg/l
yeast extract: 0.1 g/dl
L-serine: 0.5 g/dl
$CaCO_3$: 3 g/dl
(pH: 7.2)

Culturing is carried out with shaking at 30° C. for 3 days.

The quantitative determination of L-serine is carried out by paper chromatography using Toyo filter paper No. 50 with developing solvent consisting of n-butanol; acetone; water and diethyl amine [10:10:5:2 by volume].

The consumed amount of L-serine is 1.0 mg/ml. As a control, the same procedures described above the repeated except using *Nocardia butanica* ATCC 21197 and the consumed amount of L-serine is 4.6 mg/ml.

EXPERIMENT 2

The seed culturing of *Nocardia butanica* KY 7985, NRRL 11189 is carried out in the same manner as described in Experiment 1 and one ml of the resulting seed culture is inoculated into 20 ml of a fermentation medium having the following composition in a 300 ml Erlenmeyer flask:

glucose: 5 g/dl
$(NH_4)_2SO_4$: 0.2 g/dl
glycine: 0.5 g/dl
L-serine: 1 g/dl
urea: 0.2 g/dl
yeast extract: 0.5 g/dl
biotin: 50 µg/l
$KH_2PO_4$: 0.15 g/dl
$K_2HPO_4$: 0.05 g/dl
$MgSO_4 \cdot 7H_2O$: 0.05 g/dl
NaCl: 0.01 g/dl
$FeSO_4 \cdot 7H_2O$: 0.001 g/dl
$MnSO_4 \cdot nH_2O$: 0.001 g/dl
$CaCL_2 \cdot 2H_2O$: 0.001 g/dl
(pH: 7.2)

Culturing is carried out with shaking at 30° C. for 40 hours.

50 ml of the culture broth resulting from the fermentation is subjected to centrifugation to recover the microbial cells: The microbial cells are washed with isotonic-sodium chloride solution and then are suspended in 0.1 M pyrophosphate buffer solution (pH 9.0) containing $5 \times 10^{-5}$ M of pyridoxal phosphoric acid, $5 \times 10^{-4}$ M of EDTA and $10^{-4}$ M of mercapto ethanol.

The resulting suspension is subjected to disruption with ultra sonic disintegrator at 20 K.C. for 30 minutes and then to centrifugation to obtain a supernatant solution. 0.5 ml of the supernatant solution (concentration of protein: 6.0 mg/ml) and 0.5 ml of 0.1 M pyrophosphate buffer solution (pH 9.0) mentioned above containing 1.4 g/dl L-serine are combined and the mixture is allowed to stand at 37° C. for 14 hours.

The consumed amount of L-serine determined by paper chromatography described in Experiment 1 is 1.6 mg/ml. As a control, when *Nocardia butanica* ATCC 21197 is used in the same manner mentioned above, the consumed amount of L-serine is 4.2 mg/ml.

In the present invention, when the mutant is cultured in a nutrient medium containing glycine to produce L-serine in the culture liquor, the productivity of L-serine can be further enhanced by presenting phosphate at a concentration of more than 0.037 M based on the phosphate ion ($PO_4^{--}$) to the fermentation medium either at the start of the fermentation or during the growth phase of the cells.

An influence on the productivity of L-serine by the presence of a high concentration of phosphate ion in a culture medium is studied by using *Nocardia butanica* KY 7988 and the result is shown in the following Experiment 3.

EXPERIMENT 3

*Nocardia butanica* KY 7988, NRRL 11059 is inoculated into 5 ml of a fermentation medium containing 5 g/dl glucose, 1 g/dl $(NH_4)_2SO_4$, 2.5 g/dl glycine, 0.05 g/dl $K_2HPO_4$ (correspond to 0.003 M of phosphate ion), 0.15 g/dl $KH_2PO_4$ (correspond to 0.011 M of phosphate ion), 0.05 g/dl $MgSO_4 \cdot 7H_2O$, 0.001 g/dl $FeSO_4 \cdot 7H_2O$, 0.001 g/dl $MnSO_4 \cdot nH_2O$, 1 g/dl peptone, 3 g/dl $CaCO_3$ and 0–2 g/dl $Mg_3(PO_4)_2 \cdot 8H_2O$ (pH 7.2) in a large test tube. Culturing is carried out with shaking at 28° C. for 5 days, whereby L-serine is produced in a yield shown in Table 3.

Table 3

| Supplemented $Mg_3(PO_4)_2 \cdot 8H_2O$ (g/dl W/V) | Total concentration of phosphate ion (M) | Yield of L-serine (mg/ml) |
|---|---|---|
| 0 | 0.014 | 1.1 |
| 0.1 | 0.019 | 2.0 |
| 0.2 | 0.024 | 2.9 |
| 0.3 | 0.029 | 3.2 |
| 0.4 | 0.034 | 3.5 |
| 0.5 | 0.039 | 3.9 |
| 0.6 | 0.044 | 4.5 |
| 0.7 | 0.048 | 5.0 |
| 0.8 | 0.053 | 5.2 |
| 0.9 | 0.058 | 5.5 |
| 1.0 | 0.063 | 6.3 |
| 1.5 | 0.089 | 7.3 |
| 2.0 | 0.112 | 7.0 |

As is apparent from Table 3, the yield of L-serine is increased with the increasing concentration of phosphate ion (max: 6 times).

The same procedures as mentioned above are repeated except using 0–2 g/dl $MgSO_4.7H_2O$ instead of $Mg_3(PO_4)_2.8H_2O$. As a result, it is found that the increasing of the amount of $MgSO_4.7H_2O$ does not contribute toward good yield of L-serine.

Examples of the phosphate used in the present invention are $NaH_2PO_4$, $Na_2HPO_4$, $Na_3PO_4$, $KH_2PO_4$, $K_2HPO_4$, $K_3PO_4$, $NH_4.H_2PO_4$, $(NH_4)_2HPO_4$, $(NH_4)_3PO_4$, $Mg(H_2PO_4)_2$, $MgHPO_4$, $Mg_3(PO_4)_2$, $Ca(H_2PO_4)_2$, $CaHPO_4$, $Ca_3(PO_4)_2$, $Mn(H_2PO_4)_2$, $MnHPO_4$, $Mn_3(PO_4)_2$, $ZnHPO_4$, $Zn_3(PO_4)_2$, $FeHPO_4$, $Fe_3(PO_4)_2$, $Co_3(PO_4)_2$, $K(NH_4)HPO_4$, $Na(NH_4)_2PO_4$ and the like, and salt hydrate thereof.

As the phosphate, ortho-phosphate is usually used and, of course, meta-, pyro- and poly-phosphate may be used.

Further, phosphate containing substances, such as phosphate ore, industrial chemicals, for example, ion exchange resin adsorbing phosphate ion, activated carbon adsorbing phosphate ion, etc. may be used.

These phosphates are used alone or as mixtures or two or more.

The concentration of phosphates in the medium, which promotes the conversion of glycine to L-serine, is usually more than 0.037 mole/l, preferably, 0.05–0.4 mole/l.

In the present invention, in the conversion of glycine to L-serine, the productivity of L-serine can be further enhanced by supplementing to the aqueous medium, at least one additive selected from the group consisting of hydrocarbon, alcohol, ketone, ether, ester, polyalcohol and derivatives of polyalcohols.

Of course, when the mutant is cultured in a nutrient medium containing glycine to produce L-serine in the culture liquor, the productivity of L-serine can be enhanced by supplementing the additive to the medium at any time during culturing the microorganism. In this case, the additive may be usually supplemented at the time when the microorganism has completed its growth. Further, the additive may be supplemented to the medium containing glycine or after supplementing the additive to the medium, glycine may be added thereto.

Examples of additive used in the present invention are shown in Table 4.

Table 4

| | |
|---|---|
| Hydrocarbon: | ligroin, petroleum benzine, petroleum spirit, petroleum ether, cyclohexane, hexane, kerosene, hexadecane |
| Alcohol: | methanol, ethanol, n-propanol, iso-propanol, n-butanol, iso-butanol, sec-butanol, tert-butanol, n-amylalcohol, cyclohexanol, furfuryl alcohol |
| Ketone: | acetone, methyl ethyl ketone, diethyl ketone |
| Ether: | ethyl ether, isopropyl ether, n-butyl ether, 1,2-propylene oxide, 1,4-dioxane, furan, furfural, tetrahydrofuran |
| Ester: | ethyl formate, methyl acetate, ethyl acetate tributyl citrate, dioctyl phthalate, ethyl propionate, ethyl benzoate |
| Poly-alcohol: | ethylene glycol, propylene glycol, 1,3-butanediol, glycerol |
| Derivatives of poly-alcohols: | Diethylene glycol, triethylene glycol, ethylene glycol monomethyl ether, ethyl celosolve, ethylene glycol monomethyl |

Table 4-continued

| |
|---|
| acetate, ethylene glycol monobutyl ether, glycerol triacetate, glycerol ether |

These additives may be usually used at a concentration of 0.01–5% (V/V).

As to the fermentation medium employed in the present process for culturing the mutant, any synthetic or natural medium can be employed, so long as it contains a proper carbon source, a nitrogen source, inorganic materials, and trace amounts of nutrients necessary for the specific mutant.

Any carbon source and nitrogen source can be used in the medium, so long as they can be utilized by the microorganism. For example, carbohydrates such as glucose, fructose, sucrose, maltose, mannose, etc.; sugar alcohols such as sorbitol, mannitol; glycerol; starch; starch hydrolyzate liquor; molasses; etc. may be used. Further, various organic acids such as pyruvic acid, lactic acid, acetic acid, fumaric acid, gluconic acid, etc. and lower alcohols such as methanol, ethanol, glycols such as ethylene glycol, hydrocarbons such as ethane, propane, butane, n-paraffine, kelosene, etc. may also be used.

As a nitrogen source, the following substances are appropriate: ammonia; various inorganic and organic ammonium salts such as ammonium chloride, ammonium sulfate, ammonium carbonate, ammonium phosphate, ammonium nitrate, ammonium acetate, etc.; urea and other nitrogen-containing materials; and nitrogenous organic materials such as peptone, NZ-amine, meat extract, yeast extract, corn steep liquor, casein hydrolyzate, fish meal or its digested product, chrysalis hydrolyzate, etc.

As inorganic materials, monopotassium dihydrogen phosphate, dipotassium monohydrogen phosphate, magnesium sulfate, sodium chloride, ferrous sulfate, manganese sulfate, calcium carbonate, etc., may be used.

If other nutrients are necessary for the growth of the mutants, they must, of course, be present in the medium. However, it is not necessary that they be separately added to the medium so long as they are supplied to the medium together with other medium components as described above. That is, certain natural ingredients may adequately supply the specific growth promoting factors.

Culturing is carried out under aerobic conditions such as by shaking or aeration-agitation. Suitable culturing temperature is usually 20° to 40° C. It is desirable to keep the pH of the medium around neutrality throughout culturing in order to obtain a high yield, but these temperature and pH conditions are not essential for the practice of the present invention. Culturing is usually carried out for 1 to 7 days.

After the completion of the culturing, the resultant culture broth is subjected to centrifugation, filtration or the like to obtain the microbial cells. The microbial cells as they are or the cells disrupted by suitable means such as ultrasonic disintegrator, etc. are used.

When the culturing of the mutant to obtain L-serine in the culture liquor in Process (I) is carried out in the nutrient medium containing glycine, the same fermentation medium as that used to obtain microbial cells described above except containing glycine in the medium may be used, and the same culturing conditions as those described above may be used.

In this case, glycine may be presented in the nutrient medium at a concentration of 0.1–5% (W/V) either at the start of the fermentation or during the growth phase of the cells.

When the conversion is carried out according to Process (II), the cells are suspended in the phosphate buffer solution (pH 7.0) containing 0.5–20% glycine at a concentration of 5–200 mg/ml based on dry matter. Then the conversion is carried out at room temperature for 5–30 hours to accumulate L-serine in the aqueous medium.

After the completion of conversion, the microbial cells and precipitates are removed from the mixture or culture liquor by conventional methods. Then L-serine is recovered from the resultant solution by known methods, such as an ion exchange resin treatment.

Practice of certain specific embodiments of the invention is illustrated by the following representative examples.

EXAMPLE 1

Fermentation

*Nocardia butanica* KY 7985, FERM-P 3782, NRRL 11189 is used. One loopful of the seed culture obtained by culturing at 30° C. for 2 days in an agar plate of the medium containing 0.5 g/dl glucose, 0.5 g/dl yeast extract, 2 g/dl peptone, 0.5 g/dl NaCl and 2 g/dl agar (pH 7.2) is inoculated into 7 ml of a seed medium having the following composition in a large test tube (20 mm × 190 mm):
glucose: 4 g/dl
$KH_2PO_4$: 0.15 g/dl
$K_2HPO_4$: 0.05 g/dl
$MgSO_4.7H_2O$: 0.05 g/dl
urea: 0.3 g/dl
biotin: 50 µg/l
yeast extract: 0.5 g/dl
peptone: 2 g/dl
pH: 7.2

Culturing is carried out with shaking at 30° C. for 24 hours.

One ml of the resulting seed culture is inoculated into 20 ml of a fermentation medium having the following composition in a 300 ml Erlenmeyer flask:
glucose: 3 g/dl
$(NH_4)_2SO_4$: 1 g/dl
yeast extract: 0.2 g/dl
glycine: 1 g/dl
$FeSO_4.7H_2O$: 0.001 g/dl
$MnSO_4.nH_2O$: 0.001 g/dl
$MgSO_4.7H_2O$: 0.05 g/dl
$KH_2PO_4$: 0.15 g/dl
$K_2HPO_4$: 0.05 g/dl
$CaCO_3$: 3 g/dl
pH: 7.0

Culturing is carried out with shaking at 30° C. for 4 days, whereby L-serine is produced in a yield of 3.5 mg/ml.

Purification

After the completion of the culturing, one liter of culture broth resulting from the fermentation is subjected to centrifugation to remove the microbial cells and precipitates; and the resulting supernatant is passed through a column packed with 400 ml of a strongly acidic cation exchange resin, Diaion SK-1A (H+ form, manufactured by Mitsubishi Kasei Kogyo K.K., Japan) to adsorb L-serine thereon.

After the resin is washed with 1.5 l of water, the resin is subjected to elution with 0.5 N aqueous ammonia and then the fractions containing L-serine are collected and concentrated to 15 ml.

0.1 M citrate buffer solution having a pH of 3.41 is prepared by dissolving 21.01 g of citric acid in 200 ml of 1 N caustic soda, adding 110 ml of 1 N hydrochloric acid and 5 ml of thioglycol and making the resultant solution up to 1 l with water.

After the pH of the concentrate is adjusted to 3.41 with citric acid, the resulting solution is passed through a column (3.2 cm × 85 cm) packed with Diaion SK-1A (Na+ form) equilibrated with the citrate buffer solution to adsorb L-serine thereon and elution is carried out with the citrate buffer solution having a pH of 3.41 mentioned above. The column is kept at a temperature of 37.5° C. during the elution.

The fractions containing L-serine are collected and passed through a column packed with 385 ml of Diaion SK-1A (H+ form).

The resin is washed with water and subjected to elution with 0.5 N aqueous ammonia. Then, the fractions containing L-serine are collected and concentrated to 100 ml under reduced pressure. The resulting concentrate is decolorized with activated carbon and concentrated to 20 ml. The resulting solution is cooled to 5° C. and 70% (V/V) ethanol cooled to 5° C. is slowly added thereto to crystallize L-serine. The resulting crude crystals are recrystallized from alcohol, whereby 1.9 g of L-serine crystals is obtained.

As a control, the same fermentation procedures as mentioned above are repeated except using *Nocardia butanica* ATCC 21197, whereby L-serine is produced in a yield of 2.0 mg/ml.

EXAMPLE 2

The same fermentation procedures as in Example 1 are repeated except using medium containing 8 g/dl glucose and 2.5 g/dl glycine instead of 3 g/dl glucose and 1 g/dl glycine as a fermentation medium and adding 1% (V/V) prolyleneglycol 50 hours after the inoculation and then culturing is carried out for 73 hours, whereby L-serine is produced in a yield of 9.5 mg/ml.

EXAMPLE 3

In this example, *Nocardia butanica* IE-36, KY 7988, NRRL 11059 and *Nocardia butanica* KY 7985, NRRL 11189 are used.

The mutant is inoculated into 7 ml of a seed medium (pH 7.2) containing 4 g/dl glucose, 0.3 g/dl urea, 0.15 g/dl $KH_2PO_4$, 0.05 g/dl $K_2HPO_4$, 0.05 g/dl $MgSO_4.7H_2O$, 0.5 g/dl yeast extract, 2 g/dl peptone and 50 µg/l biotin in a 50 ml of large test tube (20 mm × 190 mm) and culturing is carried out at 30° C. for 24 hours. Two ml of the resulting seed culture is inoculated into 20 ml of a fermentation medium containing 5 g/dl glucose, 0.5 g/dl $NH_4Cl$, 2 g/dl glycine, 0.15 g/dl $KH_2PO_4$, 0.05 g/dl $K_2HPO_4$, 0.05 g/dl $MgSO_4.7H_2O$, 0.10 g/dl NaCl, 1 mg/dl $FeSO_4.7H_2O$, 1 mg/dl $MnSO_4.nH_2O$, 1 g/dl peptone, and 2 g/dl $Mg_3(PO_4)_2.8H_2O$, (pH 8.2) in a 300 ml Erlenmeyer flask.

Culturing is carried out with shaking at 30° C. for 5 days, whereby L-serine is produced in a yield of 8.6 mg/ml and 6.5 mg/ml respectively. The amount of the remaining glycine is 1.0 mg/ml and 6.0 mg/ml respectively.

As a control, the same procedures described above are repeated except using *Nocardia butanica* ATCC 21197, whereby L-serine is produced in a yield of 4.8 mg/ml.

After completion of the culturing of *Nocardia butanica* NRRL 11059, similar purifying procedures as described in Example 1 are repeated, whereby 5.1 g of L-serine crystals is obtained.

EXAMPLE 4

In this example, mutants shown in Table 5 are used.

As a control, *Nocardia butanica* ATCC 21197 is also used.

0.25 ml of seed culture obtained by culturing microorganisms shown in Table 5 in the same manner as described in Example 3 is inoculated into 5 ml of a fermentation medium (pH 6.1) containing 5 g/dl glucose, 1 g/dl $(NH_4)_2SO_4$, 2 g/dl glycine, 0.15 g/dl $KH_2PO_4$, 0.05 g/dl $K_2HPO_4$, 0.05 g/dl $MgSO_4.7H_2O$, 0.01 g/dl NaCl, 1 mg/dl $FeSO_4.7H_2O$, 1 mg/dl $MnSO_4.nH_2O$, 1 g/dl peptone and 3 g/dl $CaCO_3$ in a large test tube.

Culturing is carried out with shaking at 30° C. for 4 days, whereby L-serine is produced in a yield shown in Table 5.

Table 5

| Microorganism | | Yield of L-serine (mg/ml) |
|---|---|---|
| *Nocardia butanica* | KY 7983, NRRL 11187 | 4.1 |
| *Nocardia butanica* | KY 7984, NRRL 11188 | 4.1 |
| *Nocardia butanica* | KY 7986, NRRL 11190 | 2.9 |
| *Nocardia butanica* | KY 7987, NRRL 11191 | 2.8 |
| *Nocardia butanica* | KY 7985, NRRL 11189 | 2.0 |
| *Nocardia butanica* | ATCC 21197 | 0.5 |

EXAMPLE 5

In this example, microorganisms shown in Table 6 are used. The same procedures as described in Example 3 are repeated except 0.25 ml of the seed culture obtained by culturing in the same manner as described in Example 3 is inoculated into 5 ml of the same fermentation medium as described in Example 3, whereby L-serine is produced in a yield shown in Table 6.

Table 6

| Microorganism | | Yield of L-serine (mg/ml) |
|---|---|---|
| *Nocardia butanica* | KY 7989, NRRL 11192 | 7.0 |
| *Nocardia butanica* | KY 7990, NRRL 11193 | 9.5 |
| *Nocardia butanica* | KY 7991, NRRL 11194 | 9.0 |
| *Nocardia butanica* | KY 7985, NRRL 11189 | 6.0 |
| *Nocardia butanica* | ATCC 21197 | 4.5 |

EXAMPLE 6

*Nocardia butanica* IE-36, KY 7988, FERM-P No. 3768, NRRL 11059 is used. One loopful of the seed culture obtained by culturing at 30° C. for 2 days in a yeast bouillon slant containing 0.5 g/dl yeast extract, 1 g/dl peptones, 1 g/dl meat extract, 0.5 g/dl NaCl and 2 g/dl agar (pH 7.2) is inoculated into 7 ml of a seed medium containing 4 g/dl glucose, 0.15 g/dl $KH_2PO_4$, 0.05 g/dl $K_2HPO_4$, 0.05 g/dl $MgSO_4.7H_2O$, 0.5 g/dl yeast extract and 2 g/dl peptones (pH 7.2) in a 50 ml - large test tube (20 mm × 190 mm). Culturing is carried out at 30° C. for 24 hours.

One ml of the resulting seed culture is inoculated into 20 ml of a fermentation medium having the following composition in a 250 ml Erlenmeyer flask:

glucose: 5 g/dl
$(NH_4)_2SO_4$: 1 g/dl
glycine: 2.5 g/dl
$KH_2PO_4$: 0.15 g/dl (0.011 M as phosphate ion)
$K_2HPO_4$: 0.05 g/dl (0.003 M as phosphate ion)
$Mg_3(PO_4)_2.8H_2O$: 3 g/dl (0.147 M as phosphate ion)
$MgSO_4.7H_2O$: 0.05 g/dl
$FeSO_4.7H_2O$: 0.001 g/dl
$MnSO_4.nH_2O$: 0.001 g/dl
peptone: 1 g/dl
$CaCO_3$: 3 g/dl
(pH: 7.0)

Culturing is carried out with shaking at 30° C. for 5 days, whereby L-serine is produced in a yield of 8.4 mg/ml.

As a control, the same procedures described above are repeated except using the same fermentation medium excluded $Mg_3(PO_4)_2.8H_2O$ which contains 0.014 M of the phosphate ion, whereby L-serine is produced in a yield of 2.5 mg/ml. After the completion of the culturing, 1 l of culture broth is subjected to the similar purifying procedures as described in Example 1 and 4.0 g of L-serine crystals is obtained.

EXAMPLE 7

In this example, *Nocardia butanica* KY 7988 NRRL 11059 is used. The same seed culture procedures as described in Example 6 are repeated. 0.25 ml of the resulting seed culture is inoculated into 5 ml of fermentation mediums having the following compositions (Medium I and II) in a 50 ml - large test tubes.

Medium I glucose: 5 g/dl
$(NH_4)_2SO_4$: 0.4 g/dl
$KH_2PO_4$: 0.15 g/dl
$K_2HPO_4$: 0.05 g/dl
$MgSO_4.7H_2O$: 0.05 g/dl
$FeSO_4.7H_2O$: 0.001 g/dl
$MnSO_4.nH_2O$: 0.001 g/dl
glycine: 2 g/dl
peptone: 1 g/dl
$CaCO_3$: 3 g/dl
pH: 7.0

This medium contains 0.014 M of phosphate ion.

Medium II

The same composition as in Medium I except further containing phosphate shown in Table 6.

Culturing is carried out in the same manner as in Example 6, whereby L-serine is produced in a yield shown in Table 7.

Table 7

| Supplemented Phosphate g/dl (w/v) | Total concentration of phosphate ion (M) | Yield of L-serine (mg/ml) |
|---|---|---|
| $Mg_3(PO_4)_2 . 8H_2O$ (2) | 0.112 | 7.0 |
| $MgHPO_4 . 3H_2O$ (2) | 0.129 | 7.5 |

Table 7-continued

| Supplemented Phosphate g/dl (w/v) | Total concentration of phosphate ion (M) | Yield of L-serine (mg/ml) |
|---|---|---|
| $Ca_3(PO_4)_2$ (2) | 0.143 | 2.5 |
| $Mg_2(P_2O_7) \cdot 3H_2O$ (2) | 0.159 | 1.8 |
| $Zn_3(PO_4)_2 \cdot 4H_2O$ (2) | 0.102 | 2.0 |
| $K_3PO_4 \cdot nH_2O$ (2) + $MgSO_4 \cdot 7H_2O$ (3) | 0.089* | 6.0 |
| (none) | 0.014 | 1.0 |

*$K_3PO_4 \cdot nH_2O$ is calculated as tri-hydrate.

EXAMPLE 8

In this example, *Nocardia butanica* KY 7990, NRRL 11193 is inoculated into 30 ml of a seed medium containing 4 g/dl glucose, 0.15 g/dl $KH_2PO_4$, 0.05 g/dl $K_2HPO_4$, 0.05 g/dl $MgSO_4 \cdot 7H_2O$, 0.5 g/dl yeast extract, and 2 g/dl peptone (pH 7.2) in a 300 ml Erlenmeyer flask. Culturing is carried out with shaking at 30° C. for 24 hours. One ml of the resulting seed culture is inoculated into 30 ml of a fermentation medium containing 8 g/dl glucose, 1 g/dl $(NH_4)_2SO_4$, 1 g/dl peptone, 3 g/dl $Mg_3(PO_4)_2 \cdot 8H_2O$, 0.15 g/dl $KH_2PO_4$, 0.05 g/dl $K_2HPO_4$, 0.05 g/dl $MgSO_4 \cdot 7H_2O$, 0.001 g/dl $FeSO_4 \cdot 7H_2O$, and 0.001 g/dl $MnSO_4 \cdot 4H_2O$ (pH 7.2) in fifteen 300 ml of Erlenmeyer flask provided with buffle.

Culturing is carried out with shaking at 30° C. for 24 hours.

Then, 2 ml of 2 g/dl glycine solution is added to the medium and culturing is carried out for 16 hours. The resulting culture broth is combined and the mixture is subjected to centrifugation to obtain microbial cells. The resulting cells are suspended to 0.2 M phosphate buffer solution containing 2.5 g/dl glycine to obtain 60 mg/ml suspension based on dry cells. Then, the suspension is poured into 300 ml Erlenmeyer flask and the conversion is carried out with shaking at 30° C. for 20 hours, whereby L-serine is produced in a yield of 12 mg/ml.

EXAMPLE 9

In this example, *Nocardia butanica* KY 7988, NRRL 11059 is used.

The same seed culture procedures as described in Example 6 are repeated.

Two ml of the resulting seed culture is inoculated into 20 ml of a fermentation medium containing 5 g/dl glucose, 1 g/dl $(NH_4)_2SO_4$, 2.5 g/dl glycine, 0.15 g/dl $KH_2PO_4$, 0.05 g/dl $K_2HPO_4$, 0.05 g/dl $MgSO_4 \cdot 7H_2O$, 0.001 g/dl $FeSO_4 \cdot 7H_2O$, 0.001 g/dl $MnSO_4 \cdot nH_2O$, 1 g/dl peptone, and 3 g/dl $Mg_3(PO_4)_2 \cdot 8H_2O$, (pH 7.0) in a 300 ml Erlenmeyer flask. Culturing is carried out with shaking at 30° C. for 48 hours. The concentration of glucose is less than 1 g/dl after culturing.

At this time, it is understood from the following that the growth of microorganism has completed.

That is, 0.5 ml of 6 N-hydrochloride is added to 0.5 ml of culture liquor to solve the insoluble material other than microbial cells in the culture liquor. Then, the optical density of the suspension obtained by adding 24 ml of water to the resultant mixture, is measured at a wave length of 660 m$\mu$ with spectrophotometer (101 type, produced by Hitachi, Ltd.) to provide 0.27. This value is the same with that measured 2 hours before in the same manner as described abobe.

Then, the additives listed in Table 8 are supplemented at a concentration shown in Table 8 and culturing is continued for 72 hours. As a result, L-serine is produced in a yield shown in Table 8.

After the completion of the culturing, 1 l of culture liquor obtained by culturing using acetone as the additive is subjected to purification.

The similar purifying procedures as described in Example 1 are repeated and 6.2 g of L-serine crystals is obtained.

Table 8

| Additive | Concentration (% v/v) | Yield of L-serine (mg/ml) |
|---|---|---|
| ligroin | 3 | 13.0 |
| cyclohexane | 3 | 10.4 |
| methanol | 1 | 10.8 |
| ethanol | 1 | 9.0 |
| acetone | 0.5 | 11.9 |
| methylethylketone | 1 | 9.5 |
| ethyl acetate | 0.5 | 10.5 |
| methyl acetate | 1 | 10.0 |
| tributyl citrate | 0.3 | 10.0 |
| 1,4-dioxane | 2 | 9.5 |
| tetrahydrofuran | 1 | 9.8 |
| propylene glycol | 0.5 | 10.0 |
| 1,3-butanediol | 0.5 | 9.5 |
| ethyl celosolve | 0.13 | 9.0 |
| ethylene glycol monomethyl ether acetate | 0.13 | 9.0 |
| no additve | — | 8.2 |

What is claimed is:

1. A process for producing L-serine which comprises converting glycine to L-serine in an aqueous medium containing glycine in the presence of microbial cells of a mutant belonging to the species *Nocardia butanica* and capable of converting glycine to L-serine, and having a resistance to at least one metabolic antagonist selected from those of glycine, serine, methionine, glutamine, histidine, leucine, isoleucine, valine, purine, pyrimidine or folic acid, accumulating L-serine in the medium, and recovering L-serine therefrom.

2. The process according to claim 1, wherein said mutant is selected from the group consisting of *Nocardia butanica* NRRL 11059, *Nocardia butanica* NRRL 11187, *Nocardia butanica* NRRL 11188, *Nocardia butanica* NRRL 11190, *Nocardia butanica* NRRL 11191, *Nocardia butanica* NRRL 11192, *Nocardia butanica* NRRL 11193, and *Nocardia butanica* NRRL 11194.

3. The process according to claim 1, wherein conversion of the glycine to L-serine is carried out during the culturing of the mutant in a nutrient medium containing glycine.

4. The process according to claim 3, wherein said nutrient medium contains more than 0.037 mol/l of phosphate ion.

5. The process according to claim 3, wherein said nutrient medium contains 0.05–0.4 mol/l of phosphate ion.

6. The process according to claim 3, wherein said culturing is carried out at a temperature of 20°–40° C. for one to seven days.

7. The process according to claim 1, wherein said conversion is carried out in an aqueous medium containing glycine and microbial cells obtained by culturing the mutant.

8. The process according to claim 7, wherein said glycine is used at a concentration of 0.5–20%.

9. The process according to claim 1, wherein conversion of glycine to L-serine is carried out in the presence of at least one additive selected from the group consisting of hydrocarbon, alcohol, ketone, ester, ether, polyalcohol and derivative of polyalcohols.

10. The process according to claim 9, wherein the additive is in a concentration of 0.01–5% by volume per volume of the medium.

11. A process for producing L-serine which comprises converting glycine to L-serine in an aqueous medium containing glycine in the presence of microbial cells of *Nocardia butanica* NRRL 11189, accumulating L-serine in the medium and recovering L-serine therefrom.

* * * * *